(12) United States Patent
Stenzler

(10) Patent No.: US 6,432,077 B1
(45) Date of Patent: Aug. 13, 2002

(54) DEVICE AND METHOD FOR TREATMENT OF SURFACE INFECTIONS WITH NITRIC OXIDE

(75) Inventor: Alex Stenzler, Orange, CA (US)

(73) Assignee: Sensormedics Corporation, Yorba Linda, CA (US)

(*) Notice: Subject to any disclaimer, the term of this patent is extended or adjusted under 35 U.S.C. 154(b) by 63 days.

(21) Appl. No.: 09/749,022

(22) Filed: Dec. 26, 2000

(51) Int. Cl.[7] .............................................. A61M 37/00
(52) U.S. Cl. ........................ 604/23; 604/23; 604/305; 604/293
(58) Field of Search ................................ 604/308, 356, 604/309, 310, 290, 289, 304–307, 23, 293; 128/202.12, 202.13, 206.12; 424/718, 444, 434, 44, 45; 514/54, 227, 645

(56) References Cited

U.S. PATENT DOCUMENTS

| | | | | |
|---|---|---|---|---|
| 4,224,941 A | * | 9/1980 | Stivala ........................ 604/23 |
| 4,608,041 A | * | 8/1986 | Nielsen ........................ 604/23 |
| 5,427,797 A | | 6/1995 | Frostell et al. ............... 424/434 |
| 5,519,020 A | * | 5/1996 | Smith et al. ................. 424/718 |
| 5,810,795 A | * | 9/1998 | Westwood ................... 604/305 |
| 5,814,666 A | | 9/1998 | Green et al. |
| 5,845,633 A | * | 12/1998 | Psaros ................... 128/200.24 |
| 5,918,596 A | * | 7/1999 | Heinonen ............... 128/204.21 |
| 6,103,275 A | * | 8/2000 | Seitz et al. .................. 424/718 |
| 6,131,572 A | * | 10/2000 | Heinonen ............... 128/205.24 |
| 6,160,021 A | * | 12/2000 | Lerner et al. ................ 514/645 |

FOREIGN PATENT DOCUMENTS

| | | | |
|---|---|---|---|
| EP | 0 659 445 | * | 6/1995 |
| WO | WO 96/22803 | * | 8/1996 |
| WO | WO 00/30659 | | 6/2000 |

* cited by examiner

Primary Examiner—John G. Weiss
Assistant Examiner—Linh Truong
(74) Attorney, Agent, or Firm—Lyon & Lyon LLP

(57) ABSTRACT

A device for the topical delivery of nitric oxide gas to an infected area of skin includes a source of nitric oxide gas, a bathing unit, a flow control valve, and a vacuum unit. The bathing unit is adapted to surround the area of the infected skin and form a substantially air-tight seal with the skin surface. The bathing unit is also in fluidic communication with the source of nitric oxide. The flow control valve is positioned downstream of the source of nitric oxide and upstream of the bathing unit. The flow control valve controls the amount of nitric oxide gas that is delivered to the bathing unit. The vacuum unit is positioned downstream of the bathing unit and is used to withdraw gas from the bathing unit. Application of nitric oxide gas to the infected area of skin reduces pathogen levels in the infected area and promotes the healing process.

50 Claims, 3 Drawing Sheets

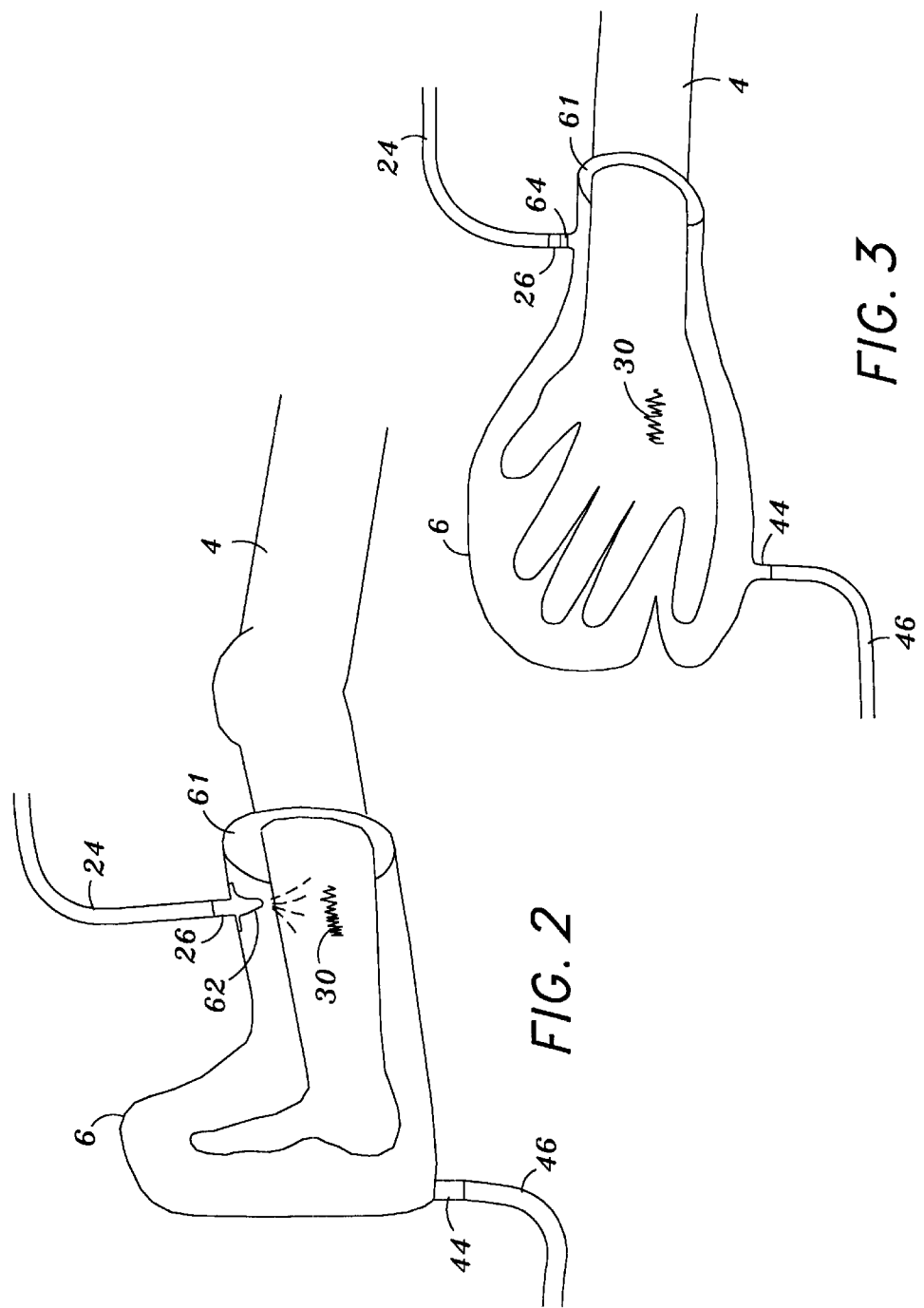

DEVICE AND METHOD FOR TREATMENT OF SURFACE INFECTIONS WITH NITRIC OXIDE

FIELD OF THE INVENTION

The field of the invention relates devices and methods for treating infected tissue. More specifically, the invention relates to devices and methods for treating surface and subsurface infections with topical nitric oxide exposure.

BACKGROUND OF THE INVENTION

The treatment of infected surface or subsurface lesions in patients has typically involved the topical or systemic administration of anti-infective agents to a patient. Antibiotics are one such class of anti-infective agents that are commonly used to treat an infected abscess, lesion, wound, or the like. Unfortunately, an increasingly number of infective agents such as bacteria have become resistant to conventional antibiotic therapy. Indeed, the increased use of antibiotics by the medical community has led to a commensurate increase in resistant strains of bacteria that do not respond to traditional or even newly developed anti-bacterial agents. Even when new anti-infective agents are developed, these agents are extremely expensive and available only to a limited patient population.

Another problem with conventional anti-infective agents is that some patients are allergic to the very compounds necessary to their treat their infection. For these patients, only few drugs might be available to treat the infection. If the patient is infected with a strain of bacteria that does not respond well to substitute therapies, the patient's life can be in danger.

A separate problem related to conventional treatment of surface or subsurface infections is that the infective agent interferes with the circulation of blood within the infected region. It is sometimes the case that the infective agent causes constriction of the capillaries or other small blood vessels in the infected region which reduces bloodflow. When bloodflow is reduced, a lower level of anti-infective agent can be delivered to the infected region. In addition, the infection can take a much longer time to heal when bloodflow is restricted to the infected area. This increases the total amount of drug that must be administered to the patient, thereby increasing the cost of using such drugs. Topical agents may sometimes be applied over the infected region. However, topical anti-infective agents do not penetrate deep within the skin where a significant portion of the bacteria often reside. Topical treatments of anti-infective agents are often less effective at eliminating infection than systemic administration (i.e., oral administration) of an anti-infective pharmaceutical.

In the 1980's, it was discovered by researchers that the endothelium tissue of the human body produced nitric oxide (NO), and that NO is an endogenous vasodilator, namely, and agent that widens the internal diameter of blood vessels. NO is most commonly known as an environmental pollutant that is produced as a byproduct of combustion. At high concentrations, NO is toxic to humans. At low concentrations, researchers have discovered that inhaled NO can be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD).

NO has also been investigated for its use as a sterilizing agent. It has been discovered that NO will interfere with or kill the growth of bacteria grown in vitro. PCT International Application No. PCT/CA99/01123 published Jun. 2, 2000 discloses a method and apparatus for the treatment of respiratory infections by NO inhalation. NO has been found to have either an inhibitory and/or a cidal effect on pathogenic cells.

While NO has shown promise with respect to certain medical applications, delivery methods and devices must cope with certain problems inherent with gaseous NO delivery. First, exposure to high concentrations of NO is toxic, especially exposure to NO in concentrations over 1000 ppm. Even lower levels of NO, however, can be harmful if the time of exposure is relatively high. For example, the Occupational Safety and Health Administration (OSHA) has set exposure limits for NO in the workplace at 25 ppm time-weighted averaged for eight (8) hours. It is extremely important that any device or system for delivering NO include features that prevent the leaking of NO into the surrounding environment. If the device is used within a closed space, such as a hospital room or at home, dangerously high levels of NO can build up in a short period of time.

Another problem with the delivery of NO is that NO rapidly oxidizes in the presence of oxygen to form $NO_2$, which is highly toxic, even at low levels. If the delivery device contains a leak, unacceptably high levels $NO_2$ of can develop. In addition, to the extent that NO oxides to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Accordingly, there is a need for a device and method for the treatment of surface and subsurface infections by the topical application of NO. The device is preferably leak proof to the largest extent possible to avoid a dangerous build up of NO and $NO_2$ concentrations. In addition, the device should deliver NO to the infected region of the patient without allowing the introduction of air that would otherwise react with NO to produce $NO_2$. The application of NO to the infected region preferably decreases the time required to heal the infected area by reducing pathogen levels. The device preferably includes a NO and $NO_2$ absorber or scrubber that will remove or chemically alter NO and $NO_2$ prior to discharge of the air from the delivery device.

SUMMARY OF THE INVENTION

In a first aspect of the invention, a device for the topical delivery of nitric oxide gas to an infected area of skin includes a source of nitric oxide gas, a bathing unit, a flow control valve, and a vacuum unit. The bathing unit is in fluid communication with the source of nitric oxide gas and is adapted for surrounding the area of infected skin and forming a substantially air-tight seal with the skin surface. The flow control valve is positioned downstream of the source of nitric oxide and upstream of the bathing unit for controlling the amount of nitric oxide gas that is delivered to the bathing unit. The vacuum unit is positioned downstream of the bathing unit for withdrawing gas from the bathing unit.

In a second aspect of the invention, the device according to the first aspect of the invention includes a controller for controlling the operation of the flow control valve and the vacuum unit.

In a third aspect of the invention, the device according to the first aspect of the invention further includes a source of dilutent gas and a gas blender. The dilutent gas and the nitric oxide gas are mixed by the gas blender. The device also includes a nitric oxide gas absorber unit that is positioned upstream of the vacuum unit. The device also includes a controller for controlling the operation of the flow control valve and the vacuum unit.

In a fourth aspect of the invention, a method of delivering an effective amount of nitric oxide to an infected area of skin includes the steps of providing a bathing unit around the infected area of skin, the bathing unit forming a substantially air-tight seal with the skin. Gas containing nitric oxide is then transported to the bathing unit so as to bathe the infected area of skin with gaseous nitric oxide. Finally, at least a portion of the nitric oxide gas is evacuated from the bathing unit.

It is an object of the invention to provide a delivery device for the topical delivery of a NO-containing gas to an infected area of skin. It is a further object of the device to prevent the NO-containing gas from leaking from the delivery device. The method of delivering an effective amount of nitric oxide gas to the infected area of skin kills bacteria and other pathogens and promotes the healing process.

BRIEF DESCRIPTION OF THE DRAWINGS

FIG. 2 illustrates a bathing unit surrounding the foot of a patient.

FIG. 3 illustrates a bathing unit surrounding the hand of a patient.

DETAILED DESCRIPTION OF THE PREFERRED EMBODIMENTS

Figure 1:
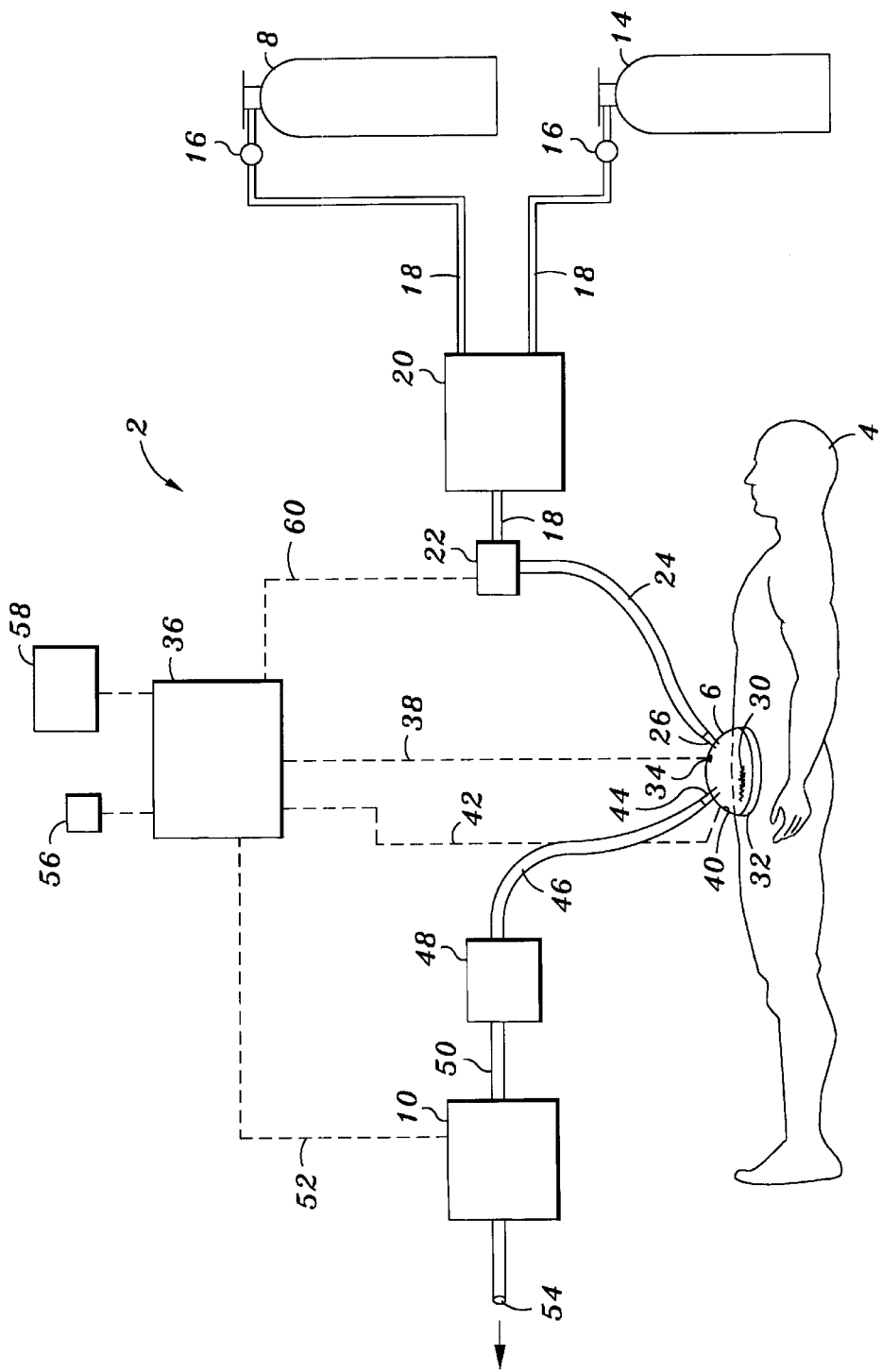
FIG. 1 illustrates a schematic representation of the NO delivery device according to one aspect of the invention.

Referring now to FIG. 1, a NO delivery device 2 is shown connected to a patient 4. In its most general sense, the NO delivery device 2 includes a bathing unit 6 that is fluidically connected to a NO gas source 8, a flow control valve 22, and a vacuum unit 10. FIG. 1 illustrates one preferred embodiment of the invention.

In FIG. 1, the NO gas source 8 is a pressurized cylinder containing NO gas. While the use of a pressurized cylinder is the preferably method of storing the NO-containing gas source 8, other storage and delivery means, such as a dedicated feed line (wall supply) can also be used. Typically, the NO gas source 8 is a mixture of $N_2$ and NO. While $N_2$ is typically used to dilute the concentration of NO within the pressurized cylinder, any inert gas can also be used. When the NO gas source 8 is stored in a pressurized cylinder, it is preferable that the concentration of NO in the pressurized cylinder fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen. Pressurized cylinders containing low concentrations of NO (i.e., less than 100 ppm NO) can also be used in accordance the device and method disclosed herein. Of course, the lower the concentration of NO used, the more often the pressurized cylinders will need replacement.

FIG. 1 also shows source of dilutent gas 14 as part of the NO delivery device 2 that is used to dilute the concentration of NO. The source of dilutent gas 14 can contain $N_2$, $O_2$, Air, an inert gas, or a mixture of these gases. It is preferable to use a gas such as $N_2$ or an inert gas to dilute the NO concentration since these gases will not oxidize the NO into $NO_2$ as would $O_2$ or air. The source of dilutent gas 14 is shown as being stored within a pressurized cylinder. While the use of a pressurized cylinder is shown in FIG. 1 as the means for storing the source of dilutent gas 14, other storage and delivery means, such as a dedicated feed line (wall supply) can also be used.

The NO gas from the NO gas source 8 and the dilutent gas from the dilutent gas source 14 preferably pass through pressure regulators 16 to reduce the pressure of gas that is admitted to the NO delivery device 2. The respective gas streams pass via tubing 18 to an optional gas blender 20. The gas blender 20 mixes the NO gas and the dilutent gas to produce a NO-containing gas that has a reduced concentration of NO. Preferably, the NO-containing gas that is output from the gas blender 20 has a concentration that is less than about 200 ppm. Even more preferably, the concentration of NO-containing gas that is output from the gas blender 20 is less than about 100 ppm.

The NO-containing gas that is output from the gas blender 20 travels via tubing 18 to a flow control valve 22. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the NO-containing gas that is input to the bathing unit 6. The NO-containing gas leaves the flow control valve 22 via flexible tubing 24. The flexible tubing 24 attaches to an inlet 26 in the bathing unit 6. The inlet 26 might include an optional one way valve 64 (see FIG. 3) that prevents the backflow of gas into the tubing 24.

Still referring to FIG. 1, the bathing unit 6 is shown sealed against the skin surface of a patient 4. The infected area 30 which can be an abscess, lesion, wound, or the like, is enclosed by the bathing unit 6. The bathing unit 6 preferably includes a seal portion 32 that forms a substantially air-tight seal with the skin of the patient 4. Substantially air-tight is meant to indicate that the NO-containing gas does not leak out of the bathing unit 6 in significant amounts (i.e., no more than about 5% of the NO-containing gas delivered to the bathing unit 6). The seal portion 32 may comprise an inflatable seal 61, such as that shown in FIGS. 2 and 3, or alternatively the seal portion 32 may comprise a flexible skirt or the like that conforms to the surface of the patient 4. The seal portion 32 also might include an adhesive portion that adheres to the skin surface of a patient 4. In other envisioned embodiments, the sealing portion 32 may merely comprise the interface of the bathing unit 6 with the surface of the patient's 4 skin.

The bathing unit 6 can be made of a virtually limitless number of shapes and materials depending on its intended use. The bathing unit 6 might be formed as a rigid structure, such as that shown in FIG. 1, that is placed over the infected area 30. Alternatively, the bathing unit 6 can be formed of a flexible, bag-like material that is inflatable over the infected area 30. FIG. 2 shows such a structure in the shape of a boot that is placed over the patient's 4 foot. FIG. 3 shows another inflatable bathing unit 6 that is formed in the shape of a mitten or glove that is worn over the patient's 4 hand.

In one preferred embodiment of the invention, the bathing unit 6 includes an NO sensor 34 that measures the concentration of NO gas within the bathing unit 6. The NO sensor 34 preferably reports this information to a controller 36 via signal line 38. An optional $NO_2$ sensor 40 can also be included within the bathing unit 6. The $NO_2$ sensor 40 preferably reports the concentration of $NO_2$ to the controller 36 via signal line 42. The sensors 40, 42 can be a chemilluminesence-type, electrochemical cell-type, or spectrophotometric-type sensor.

The bathing unit 6 also includes an outlet 44 that is used to remove gas from the bathing unit 6. The outlet 44 is preferably located away from the gas inlet 26 such that NO gas does not quickly enter and exit the bathing unit 6. Preferably, the inlet 26 and outlet 44 are located in areas of the bathing unit 6 such that the NO gas has a relatively long residence time. Flexible tubing 46 is connected to the outlet 44 and provides a conduit for the removal of gases from the bathing unit 6.

In one preferred embodiment of the invention, the flexible tubing 46 is in fluid communication with an absorber unit 48. The absorber unit 48 preferably absorbs or strips NO from the gas stream that is exhausted from the bathing unit 6. It is also preferable for the absorber unit 48 to also absorb or strip $NO_2$ from the gas stream that is exhausted from the bathing unit 6. Since these gases are toxic at high levels, it is preferable that these components are removed from the delivery device 2 prior to the gas being vented to the atmosphere. In addition, these gases can react with the internal components of the vacuum unit 10 and interfere with the operation of the delivery device 2.

The now clean gas travels from the absorbing unit 48 to the vacuum unit 10 via tubing 50. The vacuum unit 10 provides a negative pressure within the tubing 50 so as to extract gases from the bathing unit 6. The vacuum unit 10 is preferably controllable with respect to the level of vacuum or suction supplied to the tubing 50 and bathing unit 6. In this regard, in conjunction with the flow control valve 22, the amount of NO gas within the bathing unit 6 can be regulated. Preferably, the vacuum unit 10 is coupled with the controller 36 via a signal line 52. The controller 36, as discussed below, preferably controls the level of output of the vacuum unit 10. The gas then passes from the vacuum unit 10 to a vent 54 that is open to the atmosphere.

It should be understood that the absorbing unit 48 is an optional component of the delivery device 2. The gas laden with NO and $NO_2$ does not have to be removed from the gas stream if there is no concern with local levels of NO and $NO_2$. For example, the gas can be exhausted to the outside environment where high concentrations of NO and $NO_2$ will not develop. Alternatively, a recirculation system (not shown) might be used to recycle NO within the bathing unit 6.

Still referring to FIG. 1, the delivery device 2 preferably includes a controller 36 that is capable of controlling the flow control valve 22 and the vacuum unit 10. The controller 36 is preferably a microprocessor-based controller 36 that is connected to an input device 56. The input device 56 is used by an operator to adjust various parameters of the delivery device such as NO concentration, residence time of NO, pressure within the bathing unit 6, etc. An optional display 58 can also be connected with the controller 36 to display measured parameters and settings such as the set-point NO concentration, the concentration of NO within the bathing unit 6, the concentration of $NO_2$ within the bathing unit 6, the flow rate of gas into the bathing unit 6, the flow rate of gas out of the bathing unit 6, the total time of delivery, and the like.

The controller 36 preferably receives signals from sensors 34, 40 regarding gas concentrations if such sensors 34, 40 are present within the delivery device 2. Signal lines 60, 52 are connected to the flow control valve 22 and vacuum unit 10 respectively for the delivery and receipt of control signals.

In another embodiment of the invention, the controller 36 is eliminated entirely. In this regard, the flow rate of the gas into the bathing unit 6 and the flow rate of the gas out of the bathing unit 6 are pre-set or adjusted manually. For example, an operator can set a vacuum output that is substantially equal to the flow rate of the gas delivered to the bathing unit 6 via the flow control valve 22. In this manner, NO gas will be able to bathe the infected area 30 without any build-up or leaking of NO or $NO_2$ gas from the delivery device 2.

Figure 4:
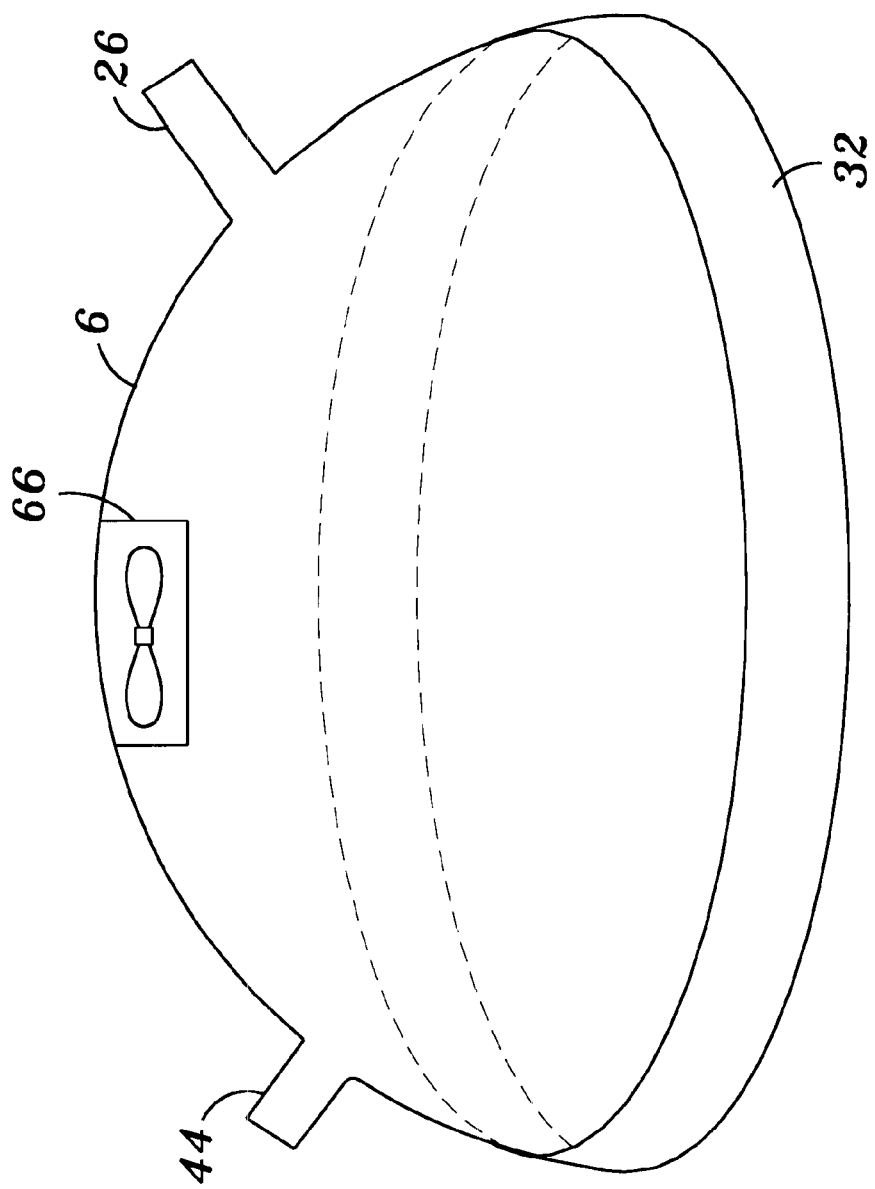
FIG. 4 illustrates a bathing unit including an agitator located therein.

FIG. 2 illustrates a bathing unit 6 in the shape of a boot that is used to treat an infected area 30 located on the leg of the patient 4. The bathing unit 6 includes an inflatable seal 61 that surrounds the leg region to make a substantially air-tight seal with the skin of the patient 4. This embodiment shows a nozzle 62 that is affixed near the inlet 26 of the bathing unit 6. The nozzle 62 directs a jet of NO gas onto the infected area 30. The jet of gaseous NO aids in penetrating the infected area 30 with NO to kill or inhibit the growth of pathogens. FIG. 3 shows another embodiment of the bathing unit 6 in the shape of a mitten or glove. The bathing unit 6 is also inflatable and contains an inflatable seal 61 that forms a substantially air-tight seal around the skin of the patient 4. FIG. 3 also shows an optional one way valve 64 located in the inlet 26. As seen in FIGS. 3 and 4, the inlet 26 and outlet 44 are located away from one another, and preferably on opposing sides of the treated area such that freshly delivered NO gas is not prematurely withdrawn from the bathing unit 6.

For treatment of an infected area 30, the bathing unit 6 is placed over the infected area 30. An air-tight seal is then formed between the skin of the patient 4 and the bathing unit 6. If the bathing unit 6 has an inflatable construction, the bathing unit 6 must be inflated with gas. Preferably, the bathing unit 6 is initially inflated only with the dilutent gas to prevent the leaking of NO and $NO_2$ from the device 2. Once an adequate air-tight seal has been established, the operator of the device initiates the flow of NO from the NO gas source 8 to the bathing unit 6. As described above, this may be accomplished manually or via the controller 36.

Once the bathing unit 6 has started to fill with NO gas, the vacuum unit 10 is turned on and adjusted to the appropriate output level. For an inflatable bathing unit 6, the output level (i.e., flow rate) of the vacuum unit 10 should be less than or equal to the flow rate of NO gas entering the bathing unit 6 to avoid deflating the bathing unit 6. In embodiments of the device where the bathing unit 6 is rigid, the vacuum unit 10 can be set to create a partial vacuum within the bathing unit 4. In this regard, the partial vacuum helps to form the air-tight seal between the skin of the patient 4 and the bathing unit 6. Of course, the vacuum unit 10 can also be set to withdraw gas at a substantially equal rate as the gas is delivered to the bathing unit 6. An effective amount of NO is delivered to the bathing unit 6 to kill pathogens and/or reduce the growth rate of the pathogens in the infected area 30. Pathogens include bacteria, viruses, and fungi.

FIG. 4 shows another embodiment of the invention in which the bathing unit 6 includes an agitator 66 that is used to create turbulent conditions inside the bathing unit 6. The agitator 66 preferably is a fan-type of mechanism but can include other means of creating turbulent conditions within the bathing unit 6. The agitator 66 aids in refreshing the infected area 30 with a fresh supply of NO gas.

While embodiments of the present invention have been shown and described, various modifications may be made without departing from the scope of the invention. The invention, therefore, should not be limited, except to the following claims, and their equivalents.

What is claimed:

1. A device for the topical delivery of nitric oxide gas to an infected area of skin, the device comprising:
    a source of nitric oxide gas;
    a bathing unit in fluid communication with the source of nitric oxide, the bathing unit being adapted for surrounding the area of the infected skin and forming a substantially air-tight seal with the skin surface;
    a flow control valve positioned downstream of the source of nitric oxide and upstream of the bathing unit for controlling the amount of nitric oxide gas delivered to the bathing unit; and
    a vacuum unit in fluid communication with the bathing unit and positioned downstream of the bathing unit for withdrawing gas from the bathing unit.

2. A device according to claim 1, further comprising a gas blender located upstream of the flow control valve for mixing nitric oxide gas with a dilutent gas.

3. A device according to claim 1, further comprising an absorber unit disposed upstream of the vacuum unit for removing nitric oxide from the gas stream.

4. A device according to claim 3, wherein the absorber unit also removes nitrogen dioxide from the gas stream.

5. The device according to claim 1, the bathing unit further comprising an inflatable seal for forming the substantially air-tight seal with the skin surface.

6. The device according to claim 1, the bathing unit being formed of an inflatable material.

7. The device according to claim 1, further comprising a gas agitator located inside the bathing unit.

8. The device according to claim 1, further comprising a gas nozzle located inside the bathing unit for directing gas at the infected area of skin.

9. The device according to claim 1, wherein the source of nitric oxide is a pressurized cylinder containing nitric oxide.

10. The device according to claim 1, further comprising a controller for controlling the operation of the flow control valve and the vacuum unit.

11. The device according to claim 1, further comprising a nitric oxide sensor located within the bathing unit.

12. The device according to claim 1, further comprising a nitrogen dioxide sensor located within the bathing unit.

13. The device according to claim 1, wherein the bathing unit comprises an inflatable bag.

14. The device according to claim 1, the bathing unit containing an effective amount of nitric oxide when positioned on the infected area of skin.

15. The device according to claim 14, the bathing unit containing less than 100 ppm of nitric oxide.

16. A device for the topical delivery of nitric oxide gas to an infected area of skin, the device comprising:
    a source of nitric oxide gas;
    a source of dilutent gas;
    a gas blender in fluid communication with the source of nitric oxide gas and the source of dilutent gas, the gas blender having an output containing a nitric oxide gas mixture;
    a flow control valve in fluid communication with the output of the gas blender;
    a bathing unit in fluid communication with the flow control valve, the bathing unit including an input and an output, the input being in fluid communication with the output of the flow control valve, wherein the bathing unit is adapted for surrounding the area of the infected skin and forming a substantially air-tight seal with the skin surface;
    a vacuum unit in fluid communication with the output of the bathing unit;
    a nitric oxide gas absorber unit disposed upstream of the vacuum unit and downstream of the bathing unit; and
    a controller for controlling the operation of the flow control valve and the vacuum unit.

17. A device according to claim 16, wherein the absorber unit also removes nitrogen dioxide from the gas stream.

18. The device according to claim 16, the bathing unit further comprising an inflatable seal for forming the substantially air-tight seal with the skin surface.

19. The device according to claim 16, the bathing unit being formed of an inflatable material.

20. The device according to claim 16, further comprising a gas agitator located inside the bathing unit.

21. The device according to claim 16, further comprising a gas nozzle located inside the bathing unit for directing gas at the infected area of skin.

22. The device according to claim 16, wherein the source of nitric oxide is a pressurized cylinder containing nitric oxide.

23. The device according to claim 16, further comprising a nitric oxide sensor located within the bathing unit.

24. The device according to claim 16, further comprising a nitrogen dioxide sensor located within the bathing unit.

25. The device according to claim 16, wherein the bathing unit comprises an inflatable bag.

26. The device according to claim 16, the bathing unit containing an effective amount of nitric oxide when positioned on the infected area of skin.

27. The device according to claim 26, the bathing unit containing less than 100 ppm of nitric oxide.

28. A method of delivering an effective amount of nitric oxide to an infected area of skin to reduce pathogen levels comprising the steps of:
    providing a bathing unit around the infected area of skin, the bathing unit forming a substantially air-tight seal with the skin;
    transporting a gas containing nitric oxide to the bathing unit so as to bathe the infected area of skin with nitric oxide; and
    evacuating at least a portion of the nitric oxide gas from the bathing unit.

29. The method according to claim 28, further comprising the step of removing at least a portion of the nitric oxide contained within the gas that is evacuated from the bathing unit.

30. The method according to claim 28, further comprising the step of controlling the flow rate of gas into and out of the bathing unit.

31. The method according to claim 28, further comprising the step of agitating the gas within the bathing unit.

32. The method according to claim 28, further comprising the step of directing the flow of gas onto the infected area of skin.

33. A device for the topical delivery of nitric oxide gas to a infected area of skin, the device comprising:
    a source of nitric oxide gas;
    a flow control valve in fluid communication with the source of nitric oxide gas;

a bathing unit in fluid communication with an output of the flow control valve, wherein the bathing unit is adapted for surrounding the infected area of skin and forming a substantially air-tight seal with the skin surface;

a vacuum unit in fluid communication with the bathing unit for removing at least a portion of the gas contained within the bathing unit; and a controller for controlling the operation of the flow control valve and the vacuum unit.

34. A device according to claim 33, further comprising a gas blender located upstream of the flow control valve for mixing nitric oxide gas with a dilutent gas.

35. A device according to claim 33, further comprising an absorber unit disposed upstream of the vacuum unit for removing nitric oxide from the gas stream.

36. A device according to claim 33, wherein the absorber unit also removes nitrogen dioxide from the gas stream.

37. The device according to claim 33, the bathing unit further comprising an inflatable seal for forming the substantially air-tight seal with the skin surface.

38. The device according to claim 33, the bathing unit being formed of an inflatable material.

39. The device according to claim 33, further comprising a gas agitator located inside the bathing unit.

40. The device according to claim 33, further comprising a gas nozzle located inside the bathing unit for directing gas at the infected area of skin.

41. The device according to claim 33, wherein the source of nitric oxide is a pressurized cylinder containing nitric oxide.

42. The device according to claim 33, further comprising a nitric oxide sensor located within the bathing unit.

43. The device according to claim 33, further comprising a nitrogen dioxide sensor located within the bathing unit.

44. The device according to claim 33, wherein the bathing unit comprises an inflatable bag.

45. The device according to claim 33, the bathing unit containing an effective amount of nitric oxide when positioned on the infected area of skin.

46. A device for the topical delivery of nitric oxide gas to an infected area of skin, the device comprising:

a source of nitric oxide gas; and a bathing unit in fluid communication with the source of nitric oxide, the bathing unit being adapted for surrounding an area of infected skin and forming a substantially air-tight seal with the skin surface.

47. The device according to claim 46, further comprising a flow control valve positioned downstream of the source of nitric oxide and upstream of the bathing unit for controlling the amount of nitric oxide gas delivered to the bathing unit.

48. The device according to claim 46, the bathing unit further comprising an outlet that is used to remove gas from the bathing unit.

49. The device according to claim 48 wherein the outlet exhausts gas to the outside environment.

50. The device according to claim 48, wherein the outlet is in communication with an absorbing unit.

* * * * *